United States Patent [19]

Boyle

[11] 4,235,908
[45] Nov. 25, 1980

[54] 4-AMINOQUINOLINE DERIVATIVES, USEFUL AS ANTI-INFLAMMATORY AGENTS

[75] Inventor: John T. A. Boyle, Maidenhead, England

[73] Assignee: John Wyeth & Brother Limited, Taplow, England

[21] Appl. No.: 28,617

[22] Filed: Apr. 9, 1979

[30] Foreign Application Priority Data

May 24, 1978 [GB] United Kingdom ............... 21915/78

[51] Int. Cl.³ .................... C07D 215/44; A61K 31/47
[52] U.S. Cl. .................................... 424/258; 546/160; 546/161
[58] Field of Search ................. 546/160, 161; 424/258

[56] References Cited

U.S. PATENT DOCUMENTS

| | | | |
|---|---|---|---|
| 3,376,195 | 4/1968 | Allais et al. | 424/258 |
| 3,632,761 | 1/1972 | Graham et al. | 424/258 X |
| 3,637,710 | 1/1972 | Wasley et al. | 546/161 |
| 3,875,165 | 4/1975 | Archibald et al. | 424/258 X |
| 3,971,787 | 7/1976 | Archibald et al. | 424/258 X |
| 3,971,789 | 7/1976 | Archibald et al. | 424/258 X |

Primary Examiner—Donald G. Daus
Assistant Examiner—Diana G. Rivers
Attorney, Agent, or Firm—Arthur E. Wilfond

[57] ABSTRACT

New 4-aminoquinoline derivatives having the formula

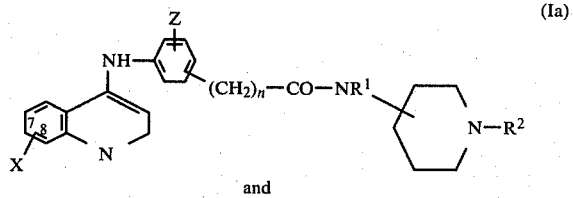

(Ia)

and

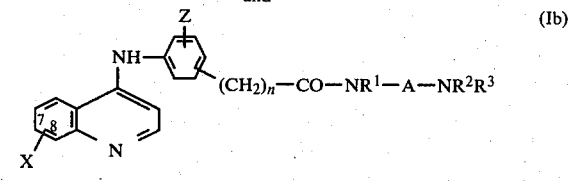

(Ib)

wherein X is halogen or trifluoromethyl at the designated 7- or 8-position; Z is hydrogen, halogen, lower alkyl, lower alkoxy, nitro, di(lower alkyl)amino or trifluoromethyl, n is from 1 to 4, $R^1$ is hydrogen or lower alkyl, $R^2$ is lower alkyl, $R^3$ is lower alkyl and A is lower alkylene, and their pharmaceutically acceptable acid addition salts show anti-inflammatory activity.

5 Claims, No Drawings

4-AMINOQUINOLINE DERIVATIVES, USEFUL AS ANTI-INFLAMMATORY AGENTS

The invention relates to novel pharmaceutically useful 4-aminoquinoline derivatives and pharmaceutical compositions containing them.

The invention provides compounds having the formula

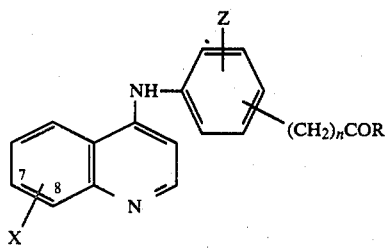

and their pharmaceutically acceptable acid additions salts, wherein X is at the designated 7- or 8-position and represents a substituent selected from trifluoromethyl and halogen, Z represents a member of the group consisting of hydrogen, halogen, lower alkyl, lower alkoxy, nitro, di(lower alkyl)amino and trifluoromethyl, n represents an integer from 1 to 4 and R represents a group selected from those having the formulae

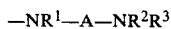   (II)

and

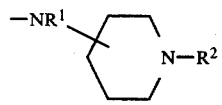   (III)

wherein $R^1$ is selected from hydrogen and lower alkyl, $R^2$ represents lower alkyl, $R^3$ represents lower alkyl and A represents lower alkylene.

By the term "lower" as used in connection with such groups as alkyl, alkoxy and alkylene, there is meant that the group contains up to 6 carbon atoms, preferably up to 4 carbon atoms.

It will be apparent to those skilled in the art that the above definition of R includes moieties possessing an asymmetric carbon atom, for instance, in the cases where A represents a branched lower alkylene group and where R represents a group of the formula

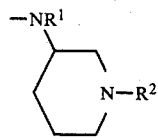   (IV)

It is to be understood that general formula I is intended to encompass both enantiomers where the compound contains an asymmetric carbon atom and also mixtures of the enantiomers, for instance, a racemic mixture of enantiomers. General methods are recorded in the literature for the resolution of enantiomers.

In the compounds of formula I, X preferably represents halogen for instance, chlorine or bromine, but may alternatively represent trifluoromethyl. X is at either one of the 7- and 8-positions shown in formula I, preferably the 7-position. Illustrative meanings of Z include hydrogen, chlorine, bromine, methyl, ethyl, propyl, butyl, methoxy, ethoxy, propoxy, butoxy, nitro, dimethylamino, methylethylamino, diethylamino and trifluoromethyl. Z is preferably hydrogen. In formula I the group —(CH₂)ₙCOR may substitute any ring position (o-, m- or p-position) relative to the [-(trifluoromethyl or halo)-4-quinoyl]amino substituent but preferably substitutes the p-position. The symbol n represents 1, 2, 3 or 4, preferably 1. $R^1$ represents hydrogen or lower alkyl, for instance, methyl, ethyl, propyl or butyl. $R^1$ preferably represents lower alkyl in formula II and preferably represents hydrogen in formula III. $R^2$ and $R^3$ represent the same or different lower alkyl groups, for instance, methyl, ethyl, propyl and butyl. In formula II A represents lower alkylene, for instance, straight chain lower alkylene such as methylene, dimethylene, trimethylene, tetramethylene or pentamethylene or branched chain lower alkylene, for example —CH(CH₃)—CH₂— or —CH₂—CH(CH₃)—CH₂—.

Examples of acid addition salts are those formed from inorganic and organic acids and include the sulphate, hydrochloride, hydrobromide, hydroiodide, nitrate, phosphate, sulphonates (for example, the methanesulphonate and p-toluenesulphonate), acetate, maleate, fumarate, tartrate, malonate, citrate and formate.

The compounds of the invention may be made by building the compound by known reactions. In particular, the amide linkage shown in formula I as —COR may be formed by acylation of an appropriate amine or an appropriate substituted aniline may be converted into a secondary amine by introducing the 7- or 8-(trifluoromethyl or halo)-4-quinolyl radical in known manner.

The invention provides a process for the preparation of a compound having formula I or a pharmaceutically acceptable acid addition salt thereof wherein (a) an amine having formula RH (where R is as defined above) or a corresponding compound with an activated amino group is acylated with a compound having the formula

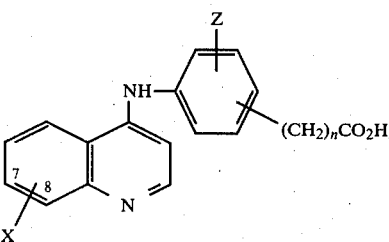   (V)

(where X, Z and n are as defined above) or a reactive derivative thereof; or (b) a substituted aniline having the formula

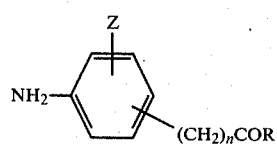   (VI)

(where Z, n and R are as defined above) is reacted with a compound having the formula

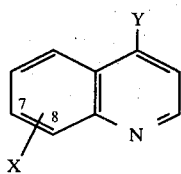

(where X is as defined above and Y represents a group or atom replaceable by nucleophilic attack by the substituted aniline of formula VI). Y is, for instance, an iodine, bromine or chlorine atom or an organosulphonyloxy group, for instance, p-toluenesulphonyloxy. Where necessary or desired, the process may also include conversion of the free base form of a compound having formula I into a pharmaceutically suitable acid addition salt thereof or conversion of an acid addition salt of a compound having formula I into the free base form.

The starting materials of formula RH and formulae V, VI and VII are known compounds or, where new, are accessible by conventional methods.

The acylation method is preferably carried out by reacting the acid having the formula V with the amine having formula RH in the presence of a condensing agent, for example, carbodiimide. As condensing agent, carbonyl diimidazole is preferably employed. Alternatively the acid having formula V may be reacted with a compound in which an amino function has been activated, for example, by forming the phosphazo derivative. The reactive acylating derivatives of the compound having formula V may be employed, for example, active esters, acyl halides, simple or mixed anhydrides and the acid azide. The acid halides, particularly the acid chloride, are especially suitable. The acylation may be performed according to regular procedures and the acylation product may be recovered from the reaction mixture by standard isolation procedures.

Compounds having formula VI are accessible in standard manner, for example, by acylation of a compound of formula RH (where R is as defined above in connection with formula I) with an acylating derivative of a nitrophenylalkanoic acid or (protected aminophenyl)alkanoic acid and subsequent reduction of the nitro group or removal of the protecting group. The reaction of the primary amine VI with the compound of formula VII may be carried out in conventional manner for amination of 4-substituted quinolines. The reaction products may be recovered from the reaction mixtures by standard isolation techniques.

The compounds of the present invention may be isolated in free base form or as an acid addition salt. Acid addition salts may be converted into the free bases in conventional manner. The free bases may be converted into acid addition salts in conventional manner, for instance, by adding ethereal hydrogen chloride to a solution of the free base where a hydrochloride salt is desired.

The compounds having formula I and their pharmaceutically acceptable acid addition salts are indicated for pharmacological usage. In particular they show anti-inflammatory activity when tested on mammals. The compounds may be tested for activity in the following test:

Adjuvant Arthritis Test for Anti-inflammatory Activity

Test Object: Male Lewis Rats

Procedure:

Polyarthritis is induced in male Lewis strain rats (150–200 gms) by the injection of a suspension of tubercle bacilli in mineral oil in the subplantar tissue of the right hind paw. Drug therapy is either begun on the day of antigen or can be started after appearance of an established arthritic syndrome (14 days). Compounds are administered daily in the form of a fine or suspension by stomach tube. Body weights, left and injected right paw volumes and occurrence of arthritic nodules on the ears, tail and front paws are determined at frequent intervals over a 14 to 21 day period. All animals are then autopsied and stress organ weights, hematology, histopathology and biochemical studies on blood proteins are done. Active compounds will either prevent or reverse the joint swelling and associated sequella of polyarthritis. The compounds of Examples 1 and 2 herein are active in the above procedure at 100 mg/kg and 50 mg/kg respectively, administered p.o.

The invention also includes pharmaceutical compositions containing as active ingredients a compound of formula (I) or a pharmaceutically acid addition salt thereof. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium, carbonate, magnesium stearate, talc, sugar, lactose, pectin, dextrin, starch, gelatin, tragacanth, methyl cellulose, sodium carboxymethyl cellulose; a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instances a compound is orally active and can be administered orally either in liquid or solid composition form.

The invention is illustrated by the following Examples:

EXAMPLE 1

2-[4-(7-Chloro-4-quinolylamino)phenyl]-N-(2-diethylaminoethyl)-N-ethyl acetamide 7.0 Grams (0.02 mole) of 2-[4-(7-chloro-4-quinolylamino)phenyl] acetic acid hydrochloride were dissolved in 150 milliliters of dimethyl sulphoxide by heating the stirred mixture to 50° C. under nitrogen. The solution was cooled to room temperature, 6.48 grams (0.04 mole) of carbonyl diimidazole were added and the mixture was stirred for 2½ hours under nitrogen. 8.64 Grams (0.06 mole) of triethylethylene diamine was added, the solution was stirred for another 2½ hrs. and poured into 500 milliliters of water. The mixture was refrigerated overnight and the resulting solid was broken up and stirred with water, but melted at room temperature. The gum was extracted with chloroform and the chloroform layer dried and evaporated to give a yellow oil, which was dissolved in ether. Addition of ethereal HCl gave 9.1 grams (89% yield) of 2-[4-(7-chloro-4-quinolylamino)phenyl]-N-(2-diethylaminoethyl)-N-ethyl acetamide dihydrochloride as a hygroscopic yellow solid, melting point 140°–142° C.

Analysis: Found: C, 58.8%; H, 6.43%; N, 10.9%. $C_{25}H_{33}Cl_3N_4O$ requires: C, 58.7%; H, 6.50%; N, 10.9%.

EXAMPLE 2

2-[4-(7-chloro-4-quinolylamino)phenyl]-N-(1-ethyl-3-piperidyl)acetamide 7.0 Grams (0.02 mole) of 2-[4-(7-chloro-4-quinolylamino)phenyl]acetic acid hydrochloride were dissolved in 150 milliliters of dimethyl sulphoxide by heating the stirred mixture to 100° C. under nitrogen. The solution was cooled to room temperature, 6.48 grams (0.04 mole) of carbonyl di-imidazole were added and the mixture was stirred for 2½ hours under nitrogen. 7.68 Grams (0.06 mole) of 3-amino-1-ethylpiperidine were added, the solution was stirred for another 2½ hours and poured into 500 milliliters of water. The mixture was refrigerated overnight and the resulting solid was broken up, stirred with water, collected and dried. The solid was dissolved in chloroform and chromatographed on an alumina column made up in chloroform. Elution with chloroform/methanol (4:1) gave 8.15 grams (92.5% yield) of 2-[4-(7-chloro-4-quinolylamino)phenyl]-N-(1-ethyl-3-piperidyl)acetamide monohydrate, melting point 160°–162° C.

Analysis: Found: C, 65.1%; H, 6.34%, N; 12.3%. $C_{24}H_{27}ClN_4O.H_2O$ requires C, 65.4%; H, 6.63%; N, 12.7%.

EXAMPLE 3

In a manner similar to Examples 1 and 2 the following acid and amines are used to make the indicated amides.

| Acid | Amine | Amide |
| --- | --- | --- |
| 2-[4-(7-Bromo-4-quinolylamino)phenyl]acetic acid | 4-Amino-1-butylpiperidine | 2-[4-(7-Bromo-4-quinolylamino)phenyl]-N-(1-butyl-4-piperidyl)acetamide |
| 2-[4-(7-Trifluoromethyl-4-quinolylamino)phenyl] acetic acid | Triethyl ethylene diamine | N-(2-Diethylaminoethyl)-N-ethyl-2-[4-(7-trifluoromethyl-4-quinolylamino)phenyl]acetamide |
| 2-[2-(7-Chloro-4-quinolylamino)phenyl]acetic acid | 3-Amino-1-ethylpiperidine | 2-[2-(7-Chloro-4-quinolylamino)phenyl]-N-(1-ethyl-3-piperidyl)acetamide |
| 4-[4-(7-Chloro-4-quinolylamino)phenyl]butyric acid | Trimethyl ethylene diamine | 4-[4-(7-Chloro-4-quinolylamino)phenyl]-N-(2-dimethylaminoethyl)-N-methylbutyramide |
| 2-[4-(8-Chloro-4-quinolylamino)phenyl]acetic acid | 3-Amino-1-ethylpiperidine | 2-[4-(8-Chloro-4-quinolylamino)phenyl]-N-(1-ethyl-3-piperidyl)acetamide |
| 2-[3-Chloro-4-(7-chloro-4-quinolylamino)phenyl] acetic acid | 3-Amino-1-ethylpiperidine | 2-[3-Chloro-4-(7-Chloro-4-quinolylamino)phenyl]-N-(1-ethyl-3-piperidyl) acetamide |
| 2-[2-Bromo-4-(7-chloro-4-quinolylamino)phenyl] acetic acid | 4-(Dimethylamino) butylamine | 2-[2-Bromo-4-(7-chloro-4-quinolylamino)phenyl]-N-(4-dimethylaminobutyl) acetamide |
| 2-[4-(7-Chloro-4-quinolylamino)-3-methylphenyl] acetic acid | 3-Amino-1-ethylpiperidine | 2-[4-(7-Chloro-4-quinolylamino)-3-methylphenyl]-N-(1-ethyl-3-piperidyl) acetamide |
| 2-[4-(7-Chloro-4-quinolylamino)-2-ethoxyphenyl] acetic acid | 3-Amino-1-ethylpiperidine | 2-[4-(7-Chloro-4-quinolylamino)-2-ethoxyphenyl]-N-(1-ethyl-3-piperidyl) acetamide |
| 2-[4-(7-Chloro-4-quinolylamino)-2-nitrophenyl] acetic acid | 3-Amino-1-ethylpiperidine | 2-[4-(7-Chloro-4-quinolylamino)-2-nitrophenyl]-N-(1-ethyl-3-piperidyl) acetamide |
| 2-[4-(7-Chloro-4-quinolylamino)-2-(trifluoromethyl) | 3-Amino-1-ethylpiperidine | 2-[4-(7-Chloro-4-quinolylamino)-2-(trifluoromethyl) |

| Acid | Amine | Amide |
|---|---|---|
| phenyl]acetic acid | | phenyl]-N-(1-ethyl-3-piperidyl)acetamide |
| 2-[4-(7-Chloro-4-quinolyl-amino)-2-(dimethylamino)phenyl]acetic acid | 3-Amino-1-ethylpiperidine | 2-[4-(7-Chloro-4-quinolyl-amino)-2-(dimethylamino)phenyl]-N-(1-ethyl-3-piperidyl)acetamide |

I claim:

1. A compound selected from those having the formula

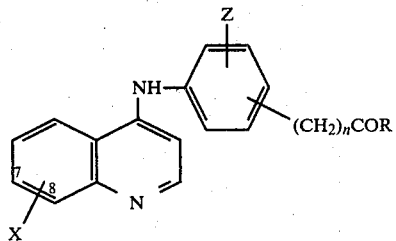

and their pharmaceutically acceptable acid addition salts, wherein X is at the designated 7- or 8-position and represents a substituent selected from trifluoromethyl and halogen, Z represents a member of the group consisting of hydrogen, halogen, lower alkyl, lower alkoxy, nitro, di(lower alkyl)amino and trifluoromethyl, n represents an integer from 1 to 4 and R represents a group selected from those having the formulae $$-NR^1-A-NR^2R^3 \quad (II)$$

and

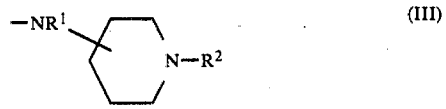

wherein $R^1$ is selected from hydrogen and lower alkyl, $R^2$ represents lower alkyl, $R^3$ represents lower alkyl and A represents lower alkylene.

2. A compound as defined in claim 1, which is 2-[4-(7-chloro-4-quinolylamino)phenyl]-N-(1-ethyl-3-piperidyl)acetamide or a pharmaceutically acceptable acid addition salt thereof.

3. A compound as defined in claim 1, which is 2-[4-(7-chloro-4-quinolylamino)phenyl]-N-(2-diethylaminoethyl)-N-ethylacetamide or a pharmaceutically acceptable acid addition salt thereof.

4. A pharmaceutical composition useful as an anti-inflammatory agent, which comprises a compound as defined in claim 1 and a pharmaceutically acceptable, non-toxic carrier.

5. A method of treating inflammation in a mammal which comprises administering to said mammal an effective anti-inflammatory amount of a compound as claimed in claim 1 or a pharmaceutically acceptable acid addition salt thereof.

* * * * *